(12) United States Patent
Murad

(10) Patent No.: US 6,515,007 B2
(45) Date of Patent: Feb. 4, 2003

(54) METHODS FOR MANAGING SCALP CONDITIONS

(76) Inventor: Howard Murad, 4265 Marina City Dr., Penthouse 11, Marina del Rey, CA (US) 90292

( * ) Notice: Subject to any disclaimer, the term of this patent is extended or adjusted under 35 U.S.C. 154(b) by 0 days.

(21) Appl. No.: 09/920,729

(22) Filed: Aug. 3, 2001

(65) Prior Publication Data

US 2002/0009423 A1 Jan. 24, 2002

Related U.S. Application Data

(62) Division of application No. 09/368,078, filed on Aug. 3, 1999, now Pat. No. 6,271,246, which is a division of application No. 09/123,484, filed on Jul. 27, 1998, now Pat. No. 6,207,694.

(51) Int. Cl.$^7$ ............................................. A61K 31/415
(52) U.S. Cl. ...................... 514/396; 514/460; 514/557; 514/721; 514/725; 514/880; 514/881
(58) Field of Search .................................. 514/396, 460, 514/557, 721, 725, 800, 801

(56) References Cited

U.S. PATENT DOCUMENTS 4,569,935 A * 2/1986 Rosenberg et al. ......... 514/252

OTHER PUBLICATIONS

WPIDS AN 1997–389337, JP 09169638 A, Jun. 30, 1997, abstract.*
MEDLINE 79172521, Orfanos et al, Hautarzt, Mar. 1979, 30(3), 124–33, abstract.*

* cited by examiner

*Primary Examiner*—Rebecca Cook
(74) *Attorney, Agent, or Firm*—Pennie & Edmonds LLP

(57) ABSTRACT

This application relates to a pharmaceutical composition for the prevention, treatment, and management of scalp conditions, such as dandruff, seborrheic dermatitis, psoriasis, folliculitis, and hair thinning including a therapeutically effective amount of an acidic component of a hydroxyacid or tannic acid, or a pharmaceutically acceptable salt thereof. A preferred anti-dandruff composition and method of managing dandruff includes a therapeutically effective amount of the acid component, a vitamin A component, and an anti-growth agent. A preferred anti-hair thinning composition and method of managing thinning hair includes a therapeutically effective amount of the acidic component, a niacin component present in an amount sufficient to locally increase blood circulation, and a 5-α reductase inhibitor. The invention also relates to a method of treating chemically processed hair by administering to a patient an amount of an acidic component of a hydroxy acid or tannic acid, or a pharmaceutically acceptable salt thereof, in an amount sufficient to essentially close the cuticle and inhibit modification of the chemically processed hair.

8 Claims, No Drawings

METHODS FOR MANAGING SCALP CONDITIONS

CROSS REFERENCE TO RELATED APPLICATIONS

This is a divisional of application Ser. No. 09/368,078, filed Aug. 3, 1999, now U.S. Pat. No. 6,271,246 which is a divisional of Ser. No. 09/123,484, filed Jul. 27, 1998, now U.S. Pat. No. 6,207,694 the contents of which are expressly incorporated herein by reference thereto.

TECHNICAL FIELD

The application relates to pharmaceutical compositions, as well as methods, to normalize skin for the prevention, treatment and management of scalp conditions.

BACKGROUND OF THE INVENTION

Human skin is a composite material of the epidermis and the dermis. The topmost part of the epidermis is the stratum corneum. This layer is the stiffest layer of the skin, as well as the one most affected by the surrounding environment. Below the stratum corneum is the internal portion of the epidermis. Below the epidermis, the topmost layer of the dermis is the papillary dermis, which is made of relatively loose connective tissues that define the micro-relief of the skin. The reticular dermis, disposed beneath the papillary dermis, is tight, connective tissue that is spatially organized. The reticular dermis is also associated with coarse wrinkles. At the bottom of the dermis lies the subcutaneous layer.

The principal functions of the skin include protection, excretion, secretion, absorption, thermoregulation, pigmentogenesis, accumulation, sensory perception, and regulation of immunological processes. These functions are detrimentally affected by, for example, dryness, yeast, and structural changes in the skin, such as due to aging and excessive sun exposure.

Many hair care products tend to include alkaline components, which tend to open pores in the scalp. While these products may improve or alter hair appearance, they may exacerbate various scalp conditions, such as dandruff, psoriasis, and seborrhea.

Various pharmaceuticals that frequently contain one or more alpha hydroxy acids, such as glycolic acid, have been used to prevent and treat certain cellular, skin, hair and other conditions. For example, U.S. Pat. No. 4,668,509 discloses polythioalkanecarboxylic anionic products and their preparation and use in cosmetic compositions and hair treatment compositions, such as shampoos.

U.S. Pat. No. 4,814,166 discloses polyanionic oligomer compounds suitable for use in keratin fiber treatment, such as hair, which may be administered in a shampoo. These compounds are alleged to hold hair with suppleness and without significant hardening of the hair.

U.S. Pat. No. 5,344,971 discloses mercapto acids, such as thiolactic acid (2-mercaptopropionic acid), that are used as reducing agents for the permanent reshaping of hair or for depilatory milks and creams.

An article entitled "Hydroxy Acids and Skin Aging" discloses the use of hydroxy and other acids as skin peels and emollients that can moisturize, stimulate, and exfoliate the skin. [Smith, W., *Soap/Cosmetics/Chemical Specialties*, pp. 54–58, 76, September, 1993.]. A study was conducted with hydroxy, keto, carboxylic, or dicarboxylic acids, including glycolic and salicylic acids, to determine long-term rejuvenating benefits. The study noted that higher pH formulations resulted in less stimulatory activity and lower irritation, and concluded that various non-hydroxy acids would be expected to deliver long-term rejuvenating benefits. Id. at 58.

One publication, WO 95/33438, discloses skin or hair care products having an agent acting cosmetically on the hair or skin, such as thioglycolic acid preferably with an ammonium salt. The agent is absorbed in a fibrous material containing amino groups, such as cellulose based-fiber containing polysilicic acid.

U.S. Pat. No. 5,422,370 discloses methods of using hydroxyacid or related compounds, such as alpha 2-hydroxypropanoic acid (lactic acid), for the treatment of wrinkles. These compounds are also disclosed to be effective for enhancing the topical effects of other cosmetic and pharmaceutical agents for treatment of conditions such as dry skin, ichthyosis, eczema, palmar and plantar hyperkeratoses, dandruff, acne, pruritis, psoriasis, Darier's disease, lichen simplex chronicus, and warts. Similarly, U.S. Pat. No. 5,547,988 discloses methods for reducing the appearance of skin changes associated with aging, such as wrinkles, by topically applying a compound of glycolic acid, lactic acid, citric acid, or a salt thereof.

U.S. Pat. No. 5,587,149 discloses improved stable emulsions of polyethylene glycol-in-oil for topical application to the skin that contain one or more water soluble active ingredients, such as Vitamin C, glycolic acid, and the like.

Despite these references, there is still a need for pharmaceutical compositions and methods for the prevention, treatment, and management of scalp conditions, such as dandruff, psoriasis, and seborrhea. The present invention advantageously provides pharmaceutical compositions, as well as methods for prevention and treatment, by administering such compositions to repair and normalize the scalp for the prevention and treatment of scalp conditions.

SUMMARY OF THE INVENTION

The present invention relates to an anti-dandruff pharmaceutical composition for administration to a scalp including an acidic component having a hydroxy acid or tannic acid, or a pharmaceutically acceptable salt thereof, in an amount sufficient to exfoliate at least a portion of the scalp, a vitamin A component in an amount sufficient to inhibit overproduction of stratum corneum on the scalp, and an anti-growth agent to inhibit fungus, yeast, bacteria, or a mixture thereof adjacent the scalp. The compositions preferably include a pharmaceutically acceptable carrier or excipient.

In one embodiment, the acidic component includes an alpha-hydroxy acid, beta-hydroxy acid or tannic acid, the vitamin A component includes retinyl palmitate, and the anti-growth agent includes clotrimazole. In a preferred embodiment, the acidic component includes at least one of glycolic acid, lactic acid, citric acid, salicylic acid, or tannic acid. In another embodiment, the acidic component is present in an amount from about 0.1 to 8 weight percent, the vitamin A component is present in an amount from about 0.01 to 1 weight percent, and the anti-growth agent is present in an amount from about 0.1 to 1.5 weight percent, of the composition. In a preferred embodiment, the pharmaceutical composition further includes at least one of a surfactant, a stabilizer, a preservative, a moisturizer, anti-inflammatory agent, anti-oxidant, and a coloring agent, which together may be present in an amount from about 10.1 to 99.1 weight percent of the composition. Also encompassed by the invention are a shampoo, cream, or gel including the pharmaceutical composition described above.

The invention also relates to an anti-hair thinning pharmaceutical composition for administration to a scalp having an acidic component including a hydroxy acid or tannic acid in an amount sufficient to exfoliate at least a portion of the scalp, or a pharmaceutically acceptable salt thereof, a niacin component present in an amount sufficient to locally increase blood circulation; and a 5-α reductase inhibitor in an amount sufficient to inhibit conversion of testosterone to dihydro-testosterone. The compositions preferably include a pharmaceutically acceptable carrier or excipient. In one embodiment, the acidic component includes an alpha-hydroxy acid, beta-hydroxy acid, or tannic acid, the niacin component includes nicotinate, and the 5-α reductase inhibitor includes at least one of finasteride or Saw Palmetto Extract. In a preferred embodiment, the acidic component includes glycolic acid, lactic acid, citric acid, salicylic acid, or tannic acid. In another embodiment, the acidic component is present in an amount from about 0.1 to 8 weight percent, the niacin component is present in an amount from about 0.01 to 1 weight percent, and the 5-α reductase inhibitor is present in an amount from about 0.1 to 1 weight percent, of the composition. In a preferred embodiment, the composition includes at least one of a surfactant, a stabilizer, a preservative, a moisturizer, anti-inflammatory agent, anti-oxidant, and a coloring agent, which together may be present in an amount from about 10.1 to 99.1 weight percent of the composition. In a preferred embodiment, the acidic component and the niacin component are adapted for topical administration and the 5-α reductase inhibitor is adapted for oral administration. The invention also encompasses a shampoo, cream, or gel including the pharmaceutical composition described above.

The invention also relates to a method of managing a scalp condition which includes administering to a patient a therapeutically effective amount of an acidic component having a hydroxy acid or tannic acid, or a pharmaceutically acceptable salt thereof, a vitamin A component, and an anti-growth agent to inhibit fungus, yeast, bacteria, or a mixture thereof that may be present adjacent the scalp. In a preferred embodiment, the scalp condition treated is at least one of dandruff, seborrheic dermatitis, psoriasis, folliculitis, or other infectious or scaling conditions.

In a preferred embodiment, the active ingredients are administered topically. In another embodiment, the administering is by at least one of a shampoo, aerosol spray, gel, paste, cream, lotion, sponge, emulsion, or ointment. In a preferred embodiment, from about 1 mg to 10,000 mg of the acidic component, vitamin A component, and anti-growth agent together are administered. In another embodiment, the acidic component, vitamin A component, and anti-growth agent are administered concurrently. In another embodiment, the acidic component, vitamin A component, and anti-growth agent are administered concurrently with at least one additional pharmaceutical composition for the prevention or treatment of a scalp condition. In another embodiment, the method further includes administering at least one of a surfactant, stabilizer, preservative, moisturizer, anti-inflammatory agent, anti-oxidant, or coloring agent. In a preferred embodiment, the acidic component includes an alpha-hydroxy acid or tannic acid, the vitamin A component includes retinyl palmitate, and the anti-growth agent includes clotrimazole.

The invention also relates to a method of managing hair thinning which includes administering to a patient a therapeutically effective amount of an acidic component having a hydroxy acid or tannic acid, or a pharmaceutically acceptable salt thereof, a niacin component present in an amount sufficient to locally increase blood supply, and a 5-α reductase inhibitor.

In a preferred embodiment, the active ingredients are administered topically. In a more preferred embodiment, the acidic component and niacin component are topically administered and the 5-α reductase inhibitor is orally administered. In another embodiment, the administering is by at least one of a shampoo, aerosol spray, gel, paste, cream, lotion, sponge, emulsion, or ointment. In a preferred embodiment, from about 1 mg to 10,000 mg of the acidic component, niacin component, and 5-α reductase inhibitor are administered. In another embodiment, the acidic component, niacin component, and 5-α reductase inhibitor are administered concurrently. In yet another embodiment, the acidic component, niacin component, and 5-α reductase inhibitor are administered concurrently with at least one additional pharmaceutical composition for the prevention or treatment of a scalp condition. In another embodiment, the method further includes administering at least one of a surfactant, stabilizer, preservative, moisturizer, anti-inflammatory agent, anti-oxidant, or coloring agent. In a preferred embodiment, the acidic component includes an alpha-hydroxy acid or tannic acid, the niacin component includes nicotinate, and the 5-α reductase inhibitor includes at least one of finasteride or Saw Palmetto Extract.

The invention further relates to a method of treating chemically processed hair having a plurality of cuticle by administering to a patient an amount of an acidic component including a hydroxy acid or tannic acid, or a pharmaceutically acceptable salt thereof, in an amount sufficient to essentially close the cuticle.

In a preferred embodiment, the administering is topically applied. In another embodiment, the administering is by at least one of a shampoo, aerosol spray, gel, paste, cream, lotion, sponge, emulsion, or ointment. In a preferred embodiment, from about 1 mg to 10,000 mg of the acidic component is administered. In another embodiment, the acidic component is administered concurrently with at least one additional pharmaceutical composition for the prevention or treatment of a scalp condition. In a preferred embodiment, the method further includes administering at least one of a surfactant, stabilizer, preservative, moisturizer, anti-inflammatory agent, anti-oxidant, or coloring agent. In another preferred embodiment, the acidic component includes an alpha-hydroxy acid or tannic acid.

The ranges of the components of the pharmaceutical composition may vary, but the active ingredients should be understood to add to 100 weight percent of the active pharmaceutical composition.

DETAILED DESCRIPTION OF THE PREFERRED EMBODIMENTS

A formulation for the prevention, treatment, and management of scalp conditions, such as dandruff, psoriasis, and seborrhea, has now been discovered. Moreover, the management of the scalp may advantageously be accomplished by the administration of the pharmaceutical composition of the present invention.

Methods for administering the compositions herein are also encompassed by the invention. Such methods include the prevention, treatment, or management of: dandruff, eczema, hair thinning, irritation, psoriasis, folliculitis, scaling, seborrhea or seborrheic dermatitis, all while reducing environmental damage to the hair and scalp and maintaining color in chemically processed hair as advantageous benefits. The compositions may be prepared in high concentrations for administration by professionals in a salon, as well as lower concentrations that are safer for home use. The methods of the present invention also include administering mono- or poly-hydroxy or tannic acids for treating chemically processed hair, which advantageously closes or essentially closes the hair cuticle. The closing of the cuticle helps "lock in" hair color to prevent fading or washout of the chemically processed hair.

The pharmaceutical composition includes the combination of a number of different components that interact to provide the desired improvements to the skin. The compositions include an acidic component including one or more mono- or poly-hydroxy acids or tannic acid, a mixture thereof, or a pharmaceutically acceptable salt or ester thereof One of ordinary skill in the art will be readily able to select and prepare suitable mono- or poly-hydroxy acids for use in the composition of the invention, for example, alkyl hydroxycarboxylic acids, aralkyl and aryl hydroxycarboxylic acids, polyhydroxy-carboxylic acids, and hydroxy-polycarboxylic acids. To assist one of ordinary skill in the art, some preferred mono- or poly-hydroxy acids include: 2-hydroxyacetic acid (glycolic acid); 2-hydroxypropanoic acid (lactic acid); 2-methyl 2-hydroxypropanoic acid; 2-hydroxybutanoic acid; phenyl 2-hydroxyacetic acid; phenyl 2-methyl 2-hydroxyacetic acid; 3-phenyl 2-hydroxyacetic acid; 2,3-dihydroxypropanoic acid; 2,3,4-trihydroxybutanoic acid; 2,3,4,5,6-pentahydroxyhexanoic acid; 2-hydroxydodecanoic acid; 2,3,4,5-tetrahydroxypentanoic acid; 2,3,4,5,6,7-hexahydroxyheptanoic acid; diphenyl 2-hydroxyacetic acid; 4-hydroxymandelic acid; 4-chloromandelic acid; 3-hydroxybutanoic acid; 4-hydroxybutanoic acid; 2-hydroxyhexanoic acid; 5-hydroxydodecanoic acid; 12-hydroxydodecanoic acid; 10-hydroxydecanoic acid; 16-hydroxyhexadecanoic acid; 2-hydroxy-3-methylbutanoic acid; 2-hydroxy4-methylpentanoic acid; 3-hydroxy-4-methoxymandelic acid; 4-hydroxy-3-methoxymandelic acid; 2-hydroxy-2-methylbutanoic acid; 3-(2-hydroxphenyl) lactic acid; 3-(4-hydroxyphenyl) lactic acid; hexahydromandelic acid; 3-hydroxy-3-methylpentanoic acid; 4-hydroxydecanoic acid; 5-hydroxydecanoic acid; aleuritic acid; 2-hydroxypropanedioic acid; 2-hydroxybutanedioic acid; erythraric acid; threaric acid; arabiraric acid; ribaric acid; xylaric acid; lyxaric acid; glucaric acid; galactaric acid; mannaric acid; gularic acid; allaric acid; altraric acid; idaric acid; talaric acid; 2-hydroxy-2-methylbutanediodic acid; citric acid, isocitric acid, agaricic acid, quinic acid, glucoronic acid, glucoronolactone, galactoronic acid, galactoronolactone, uronic acids, uronolactones, ascorbic acid, dihydroascorbic acid, dihydroxytartaric acid, tropic acid, ribonolactone, gluconolactone, galactonolactone, gulonolactone, mannonolactone, citramalic acid; pyruvic acid, hydyroxypyruvic acid, hydroxypyruvic acid phosphate and esters thereof; methyl pyruvate, ethyl pyruvate, propyl pyruvate, isopropyl pyruvate; phenyl pyruvic acid and esters thereof; methyl phenyl pyruvate, ethyl phenyl pyruvate, propyl phenyl pyruvate; formyl formic acid and esters thereof; methyl formyl formate, ethyl formyl formate, propyl formyl formate; benzoyl formic acid and esters thereof; methyl benzoyl formate, ethyl benzoyl formate and propyl benzoyl formate; 4-hydroxybenzoyl formic acid and esters thereof; 4-hydroxyphenyl pyruvic acid and esters thereof; and 2-hydroxyphenyl pyruvic acid and esters thereof. The hydroxy acids are more preferably selected from one or more alpha-hydroxy acids or beta-hydroxy acids, most preferably from glycolic, lactic, citric, or salicylic acid. It should be understood that one or more derivatives of the above acidic component, such as esters or lactones thereof, are also suitably used. One of ordinary skill in the art will also understand that various hydroxy acids described in U.S. Pat. Nos. 5,547,988 and 5,422,370 are also suitable for use in the compositions and methods of the invention. The acidic component is present in the composition and methods in an amount sufficient to exfoliate, i.e., remove dead or dying skin cells, from at least a portion of the scalp. The acidic component is typically present in an amount from about 0.1 to 8 weight percent, preferably about 0.5 to 5 weight percent, more preferably from about 1 to 3 weight percent of the composition. For example, the acidic component may be from about 0.2 to 10 weight percent GLYPURE, which contains 70 weight percent glycolic acid, in combination with about 0.1 to 0.3 weight percent salicylic acid.

Compositions and methods for managing dandruff, seborrheic dermatitis, psoriasis, folliculitis, and other scaling or infectious scalp conditions, also include a vitamin A component and an anti-growth agent. The vitamin A component preferably is retinyl palmitate. The vitamin A component is present in an amount sufficient to normalize epidermal growth by inhibiting overproduction of the stratum corneum. The vitamin A component is typically present in an amount from about 0.01 to 1 weight percent, preferably 0.05 to 0.8 weight percent, and more preferably 0.1 to 0.5 weight percent of the composition. Vitamin A is toxic at high levels, such that no more than 400,000 IU should be cumulatively ingested per day for greater than six months.

Any pharmaceutically acceptable anti-growth agent may be used, preferably an antifungal agent, antiyeast agent, or antibacterial agent, more preferably triclosan, clotrimazole, and the like, and mixtures thereof. The anti-growth agent is typically present in an amount from about 0.1 to 1.5 weight percent, preferably from about 0.3 to 1.2 weight percent, and more preferably from about 0.5 to 1 weight percent of the composition. The anti-growth agent may inhibit the fungus *Pityrosporum ovale*, which tends to be present in patients having dandruff or seborrheic dermatitis. Together, the acidic component, Vitamin A component, and anti-growth agent facilitate exfoliation of dead skin, facilitate hydration of the scalp, and inhibit the presence of yeast or fungus, such as all of which assist in the management of dandruff, psoriasis, folliculitis, seborrheic dermatitis, and other inflammatory or scaling conditions of the scalp.

Compositions and methods for the management of thinning hair include a niacin component and a 5-α reductase inhibitor, in addition to the acidic component. The niacin component (vitamin $B_3$) may be any pharmaceutically acceptable niacin component, preferably niacinamide or nicotinate, more preferably nicotinate. The niacin component should be present in an amount sufficient to facilitate improved blood circulation in the scalp, which may help inhibit hair loss. Thus, the niacin component is typically present in an amount from about 0.01 to 1 weight percent, preferably from about 0.05 to 0.8 weight percent, and more preferably from about 0.1 to 0.5 weight percent of the composition.

Any pharmaceutically acceptable 5-α reductase inhibitor may be used in the anti-hair thinning compositions, such as finasteride, Saw Palmetto Extract (*Serenoa repens*), MK-386, LY191704, turosteride, PNU 157706, FK-143, GG-745, ONO-9302, and the like, and mixtures thereof. A preferred 5-α reductase inhibitor is Saw Palmetto Extract (Serenoa Serrulata). The 5-α reductase inhibitor is typically present in an amount sufficient to inhibit conversion of testosterone in the scalp to dihydro-testosterone, the latter of which is believed to increase hair thinning. The 5-α reductase inhibitor is typically present in an amount from about 0.01 to 1 weight percent, preferably about 0.05 to 0.5 weight percent, and more preferably about 0.08 to 0.2 weight percent of the composition. The hydroxy acid, niacin component, and 5-α reductase inhibitor together facilitate exfoliation of dead skin, improve blood circulation, and ultimately inhibit and/or reduce hair loss.

In a preferred embodiment, the compositions all contain one or more surfactants, stabilizers, preservatives, moisturizers, coloring agents, anti-inflammatory agents, anti-oxidants, water, and the like, and mixtures thereof. The water used is preferably deionized water. It should be understood that water includes the remainder of a given composition after other ingredients are determined. Although any pharmaceutically acceptable surfactant, stabilizer, preservative, moisturizer, or coloring agent may be used, certain compounds or mixtures are preferred as discussed below.

Preferred surfactants, including both the foaming and non-foaming type, include sodium laureth sulfate, disodium cocoamphodiacetate, and the like, and mixtures thereof. The surfactant component may be present in an amount from about 10 to 90 weight percent, preferably about 20 to 80, and more preferably about 30 to 70 weight percent of the composition.

A preferred stabilizer includes glycol stearate. The stabilizer, when used, is typically present in an amount from about 0.1 to 5 weight percent of the composition.

Preferred preservatives include tetrasodium ethylenediamine tetraacetic acid (EDTA), methylparaben, benzophenone-4, methylchloroisothiazolinone, methylisothiazolinone, and the like, and mixtures thereof. Preservatives, when used, are typically present in an amount from about 0.01 to 6 weight percent, preferably about 0.05 to 4 weight percent, and more preferably from about 0.1 to 2 weight percent.

Preferred moisturizers include wheat protein (e.g., laurdimonium hydroxypropyl hydrolyzed wheat protein), hair keratin amino acids, sodium peroxylinecarbolic acid, panthenol, tocopherol (Vitamin E), dimethicone, and the like, and mixtures thereof. Sodium chloride may also be present, particularly when hair keratin amino acids are included as a moisturizer. Moisturizers are typically present in an amount from about 0.01 to 2 weight percent, preferably about 0.05 to 1.5 weight percent, more preferably from about 0.1 to 1 weight percent of the composition.

Preferred coloring agents include FD&C Green No. 3, Ext. D&C Violet No. 2, FD&C Yellow No. 5, FD&C Red No. 40, and the like, and mixtures thereof. The coloring agents are preferably used, and when used are typically present in an amount from about 0.001 to 0.1 weight percent, and preferably from about 0.005 to 0.05 weight percent of the composition.

Preferred anti-inflammatory agents include any pharmaceutically acceptable compounds suitable for administration orally or topically, preferably allantoin. The anti-inflammatory agents, when present, are used in an amount sufficient to inhibit or reduce inflammation, preferably in an amount from about 0.1 to 2 weight percent, preferably from about 0.3 to 1.5 weight percent, and more preferably from about 0.3 to 1 weight percent of the composition.

Anti-oxidants of both the enzymatic and non-enzymatic type may be included in the compositions and methods of the invention. For example, superoxide dismutase (SOD), catalase, and glutathione peroxidase are natural enzymatic anti-oxidants used by the body that may be supplemented with the compositions herein. Suitable non-enzymatic anti-oxidants include such as Vitamin E (e.g. tocopherol), Vitamin C (ascorbic acid), carotenoids, Echinacoside and caffeoyl derivatives, oligomeric proanthocyanidins or proanthanols (e.g., grape seed extract), silymarin (e.g., milk thistle extract, *Silybum marianum*), ginkgo biloba, green tea polyphenols, and the like, and mixtures thereof. Carotenoids are powerful anti-oxidants, and they include beta-carotene, canthaxanthin, zeaxanthin, lycopen, lutein, crocetin, capsanthin, and the like. Indeed, any pharmaceutically acceptable compounds suitable for administration orally or topically may be used as an anti-oxidant in the compositions. Preferably, the anti-oxidant component includes Vitamin E, Vitamin C, or a carotenoid. The anti-oxidant component, when used, is present in an amount sufficient to inhibit or reduce the effects of free-radicals at the scalp. The anti-oxidant component may be present in an amount from about 0.001 to 1 weight percent, preferably from about 0.01 to 0.5 weight percent of the composition.

Application of chemicals to the hair, such as for coloring or other hair treatment, requires the cuticles to be opened, which may be accomplished by using any of a variety of alkaline components suitable for application to the hair. It should be understood that the application of the acidic component, however, will close or essentially close the cuticle incidental to the methods of managing scalp conditions, as discussed herein. Thus, chemical processing of the hair is rendered more difficult after application of the compositions of the present invention. However, when it is desired to specifically protect chemically processed hair, the compositions herein may be administered subsequent to, preferably immediately subsequent to, chemical processing of the hair. By "immediately" it is meant that the compositions herein are administered within 4 hours, preferably within 1 hour, and more preferably within 30 minutes of the chemical processing. Thus, in a preferred embodiment for protecting chemically processed hair, a patient may optionally have their hair conventionally shampooed and rinsed, chemically processed, and then have the compositions of the invention administered to protect the processing by closing or essentially closing the cuticle.

The term "scalp conditions" as used herein means conditions including dandruff, eczema, hair thinning, irritation, psoriasis, scaling, folliculitis, seborrhea or seborrheic dermatitis, and the like.

The terms "managing" or "management" as used herein includes one or more of the prevention, treatment, or modification of a condition.

The term "environmental damage" as used herein means weather or other damage to the scalp or hair from exposure to one or more of water, sun, pollution, overdrying, overteasing, and the like.

The term "therapeutically effective amount" means that amount of the pharmaceutical composition that provides a therapeutic benefit in the treatment, prevention, or management of scalp conditions.

The magnitude of a prophylactic or therapeutic dose of the composition in the acute or chronic management of scalp conditions will vary with the severity of the condition to be treated and the route of administration. The dose, and perhaps the dose frequency, will also vary according to the age, body weight, and response of the individual patient. In general, a preferred topical daily dose range, in single or divided doses, for the conditions described herein should be from about 1 mg to 20,000 mg, more preferably about 2,000 mg to 16,000 mg, and most preferably about 6,000 mg to 10,000 mg of the active components (i.e., excluding excipients and carriers).

Those of ordinary skill in the art will also understand that topical effectiveness of pharmaceuticals requires percutaneous absorption and bioavailability to the target site. Thus, the compositions and methods of the invention require penetration through the stratum corneum into the epidermal layers, as well as sufficient distribution to the sites targeted for pharmacologic action.

It is further recommended that children, patients aged over 65 years, and those with impaired renal or hepatic function initially receive low doses, and that they then be titrated based on individual response(s) or blood level(s). It may be necessary to use dosages outside these ranges in some cases, as will be apparent to those of ordinary skill in the art. Further, it is noted that the clinician or treating physician will know how and when to interrupt, adjust, or terminate therapy in conjunction with individual patient response.

The term "unit dose" is meant to describe a single dose, although a unit dose may be divided, if desired. About 1 to 2 unit doses of the present invention are typically administered per day, preferably about 1 dose per day.

Any suitable route of administration may be employed for providing the patient with an effective dosage of the composition according to the methods of the present invention, including oral, intraoral, rectal, parenteral, topical, epicutaneous, transdermal, subcutaneous, intramuscular, intranasal, sublingual, buccal, intradural, intraocular, intrarespiratory, or nasal inhalation and like forms of administration. Topical administration is generally preferred for the compositions and methods of the invention, although oral administration is preferred for the 5-α reductase inhibitor. Suitable dosage forms include dispersions, suspensions, solutions, aerosols, sponges, cotton applicators, and the like, with topical dosage forms such as shampoos being preferred. A sunscreen dosage form is one preferred embodiment for methods and compositions for the management of thinning hair, since extra protection is required when more scalp is exposed to harmful ultraviolet radiation. In a sunscreen dosage form, it is preferred to include benzophenone-4, which provides the scalp with some sunscreen protection factor from ultraviolet radiation.

The pharmaceutical compositions used in the methods of the present invention include the active ingredients described above, and may also contain pharmaceutically acceptable carriers, excipients and the like, and optionally, other therapeutic ingredients.

The term "pharmaceutically acceptable salt" refers to a salt prepared from pharmaceutically acceptable non-toxic acids or bases including inorganic or organic acids. Examples of such inorganic acids are hydrochloric, hydrobromic, hydroiodic, sulfuric, and phosphoric. Appropriate organic acids may be selected, for example, from aliphatic, aromatic, carboxylic and sulfonic classes of organic acids, examples of which are formic, acetic, propionic, succinic, glycolic, glucoronic, maleic, furoic, glutamic, benzoic, anthranilic, salicylic, phenylacetic, mandelic, embonic (pamoic), methanesulfonic, ethanesulfonic, pantothenic, benzenesulfonic, stearic, sulfanilic, algenic, and galacturonic. Examples of such inorganic bases, for potential salt formation with the sulfate or phosphate compounds of the invention, include metallic salts made from aluminum, calcium, lithium, magnesium, potassium, sodium, and zinc. Appropriate organic bases may be selected, for example, from N,N-dibenzylethylenediamine, chloroprocaine, choline, diethanolamine, ethylenediamine, meglumaine (N-methylglucamine), and procaine.

The compositions for use in the methods of the present invention may include components such as suspensions, solutions and elixirs; aerosols; or other suitable carriers such as starches, sugars, microcrystalline cellulose, diluents, granulating agents, lubricants, binders, disintegrating agents, and the like, with the topical preparations being preferred.

Because of its ease of administration, shampoo represents the most advantageous topical dosage unit form, in which case liquid pharmaceutical carriers may be employed in the composition. These shampoos may be prepared as rinse-off or leave-on after-shampoo products, as well as two stage treatment shampoos. Additionally, the composition may also be prepared as a stand-alone conditioner or pre- or post-shampoo conditioner. In a preferred embodiment, the compositions are administered as a shampoo, then as a conditioner after the shampoo is rinsed away, and optionally in a higher concentration form, such as a gel, subsequently thereto. Each of these forms is well understood by those of ordinary skill in the art, such that dosages may easily be prepared to incorporate the pharmaceutical composition of the invention.

Pharmaceutical compositions for use in the methods of the present invention suitable for topical administration may be presented as discrete units including aerosol sprays, each containing a predetermined amount of the active ingredient, as a powder, stick, or granules, as creams (e.g., a conditioner), pastes, gels, lotions (e.g., a sunscreen), syrups, or ointments, on sponges or cotton applicators, or as a solution or a suspension in an aqueous liquid, a non-aqueous liquid, an oil-in-water emulsion, or a water-in-oil liquid emulsion. Such compositions may be prepared by any of the methods of pharmacy, but all methods include the step of bringing into association the carrier(s) with the active ingredient, which constitutes one or more necessary ingredients. In general, the compositions are prepared by uniformly and intimately admixing the active ingredient with liquid carriers or finely divided solid carriers or both, and then, if necessary, shaping the product into the desired presentation.

Other suitable dosage forms include tablets, troches, capsules, patches, gel caps, magmas, lozenges, plasters, discs, suppositories, nasal or oral sprays, and the like. Tablets, capsules, and gel caps are the preferred oral dosage unit form for the 5-α reductase inhibitor, in which case solid pharmaceutical carriers may be employed. If desired, tablets may be coated by standard aqueous or nonaqueous techniques.

In addition to the common dosage forms set out above, the compound for use in the methods of the present invention may also be administered by controlled release means and/or delivery devices such as those described in U.S. Pat. Nos. 3,845,770; 3,916,899; 3,536,809; 3,598,123; and 4,008,719, the disclosures of which are expressly incorporated herein by reference thereto.

For example, a tablet may be prepared by compression or molding, optionally, with one or more accessory ingredients. Compressed tablets may be prepared by compressing in a suitable machine the active ingredient in a free-flowing form such as powder or granules, optionally mixed with a binder, lubricant, inert diluent, surface active or dispersing agent. Molded tablets may be made by molding, in a suitable machine, a mixture of the powdered compound moistened with an inert liquid diluent.

Desirably, each unit dose, e.g., shampoo, contains from about 1 mg to 2,000 mg of the active ingredient, preferably about 200 mg to 1,600 mg, and more preferably about 600 mg to 1,000 mg of the composition.

EXAMPLES

The invention is further defined by reference to the following examples describing in detail the preparation of the compound and the compositions used in the methods of the present invention, as well as their utility. The examples are representative, and they should not be construed to limit the scope of the invention.

Example 1

Shampoo for Dandruff Treatment

A pharmaceutical composition according to the invention may be prepared in the form of a shampoo formulated for dandruff management as set forth below:

Deionized water may be metered into the processing tank and high speed mixing subsequently begun. Guar hydroxypropyltrimonium and glycolic acid are added one at a time. Once the guar component is completely dispersed, the mixture is heated to 75° C. The remaining Part A ingredients are then added and mixed until all the solids are dissolved. The mixture is cooled to 60° C. and the Part B ingredients are added and mixed until uniform. The mixture is then cooled to 50° C. In a separate vessel, Part C is premixed until homogeneous, then added to the mixture of Parts A & B. Parts A, B, and C are mixed until uniform. The Part D ingredients are added and mixed until uniform, then cooled to 40° C. Premixed Part E is added and mixed until uniform, the Part F ingredients are added and mixed, and the composition is then cooled to 35° C. The appearance should be an aqua blue, opaque, pearlized, semi-viscous liquid having a pH at 25° C. of between 4 to 5 and a viscosity between 5,000 to 9,000 cps (RVT:#4 @ 10 rpm @25° C.).

| | Ingredient | Trade Name/Supplier | % by Weight |
|---|---|---|---|
| Part A | Deionized Water | N/A | 47 |
| | Guar Hydroxypropyltrimonium Chloride | JAGUAR C-13S | 0.1 |
| | Glycolic Acid | GLYPURE-70% Glycolic Acid | 1.5 |
| | Methylparaben | Methylparaben | 0.2 |
| | Sodium Laureth Sulfate | CARSONOL SLES-2 | 28 |
| | Glycol Distearate | LEXEMUL EGDS | 1 |
| | Cocamidopropyl Betaine | LONZAINE C | 5 |
| Part B | Lauramide Diethanolamine (DEA) | MONAMID 716 | 2 |
| Part C | Salicylic Acid | Salicylic Acid, powdered, USP | 1.2 |
| | Sodium Laureth Sulfate | CARSONOL SLES-2 | 10 |
| Part D | Allantoin | ALLANTOIN | 0.1 |
| | Panthenol | DL-PANTHENOL 50% | 0.3 |
| | Dimethicone (and) Laureth-4 and Laureth-23 | DOW CORNING 1664 | 0.05 |
| Part E | Clotrimazole | Clotrimazole, USP | 0.5 |
| | Alcohol (denatured) | SD ALCOHOL 40, Anhydrous | 1.5 |
| Part F | Glycolic Acid | GLYPURE-70% Glycolic Acid | 0.15 |
| | Phenoxyethanol | Phenoxyethanol | 0.7 |
| | Methylchloroisothiazolinone and Methylisothiazolinone | KATHON CG | 0.05 |
| | Retinyl Palmitate | Vitamin A Palmitate, type P1.7 | 0.02 |
| | Tocopherol | Vitamin E USP, #60525 | 0.02 |
| | Benzophenone-4 | UVINUL MS-40 | 0.1 |
| | FD&C Green No. 3 (CI 42053) | FD&C Green No. 3 (1.0% Solution) | 0.02 |
| | Ext. D&C Violet No. 2 (CI 60730) | Ext. D&C Violet No. 2 (0.10% Solution) | 0.2 |
| | Fragrance (Parfum) | Natural Fragrance - Haarmann & Reimer #A40758/778926 | 0.3 |
| | | | 100% |

JAGUAR C-13S is commercially available from Rhone-Poulenc N. American Chemicals of Cranbury, NJ;
GLYPURE is commercially available from DuPont of Wilmington, DE;
CARSONOL SLES-2 and LONZAINE C are commercially available from Lonza, Inc. of Fair Lawn, NJ;
LEXEMUL EGDS is commercially available from Inolex Chemical Co. of Philadelphia, PA;
MONAMID 716 is commercially available from Mona Industries, Inc. of Paterson, NJ;
Allantoin is commercially available from ISP Corp. of Bound Brook, NJ;
DL-PANTHENOL and UVINUL MS-40 are commercially available from BASF Corp. of Budd Lake, NJ;
DOW CORNING 1664 is commercially available from Dow Corning Corp. of Auburn, MI;
KATHON CG is commercially available from Rohm & Haas Co. of Philadelphia, PA;
FD&C Green No. 3 and Ext. D&C Violet No. 2 are commercially available from Hilton-Davis Co. of Cincinnati, OH; and
Natural Fragrance #A4-758/778926 is commercially available from Haarmann & Reimer of Holzminden, Germany (subsidiary of Bayer Aktiengesellschaft).

Example 2

Shampoo for Thinning Hair

A pharmaceutical composition according to the invention may be prepared in the form of a shampoo formulated for management of thinning hair as set forth below:

|  | Ingredient | Trade Name/Supplier | % by Weight |
|---|---|---|---|
| Part A | Deionized water | N/A | 51.9 |
|  | Polyquaternium-10 | UCARE Polymer JR-125 | 0.15 |
|  | Glycolic Acid | GLYPURE-70% Glycolic Acid | 1 |
|  | Methylparaben | N/A | 0.2 |
|  | Sodium Laureth Sulfate | CARSONOL SLES-2 | 35 |
|  | Glycol Stearate | LEXEMUL EGMS | 0.75 |
|  | Phytantriol | N/A | 0.1 |
|  | Sodium Lauroyl Sarcosinate | HAMPOSYL L-30 | 1.5 |
|  | Cocamidopropyl Betaine | LONZAINE C | 5 |
|  | Panthenyl Ethyl Ether | Ethyl Panthenol | 0.2 |
|  | Tetrasodium Ethylene-Diamine-Tetraacetic Acid (EDTA) | HAMP-ENE 220 | 0.03 |
|  | Benzophenone-4 | Uvinul MS-40 | 0.1 |
| Part B | Lauramide Diethanolamine | MONAMID 716 | 2.2 |
| Part C | Lactamide Monoethanolamine (MEA) | PARAPEL LAM-100 | 0.6 |
|  | Sodium Peroxylinecarbolic Acid (PCA) | AJIDEW N-50 | 0.4 |
|  | Hair Keratin Amino Acids and Sodium Chloride | CROTEIN HKP | 0.1 |
| Part D | Saw Palmetto (*Serenoa Serrulata*) Extract | Saw Palmetto Berry Glycolic Extract | 0.1 |
|  | Methylchloroisothiazolinone and Methylisothiazolinone | KATHON CG | 0.05 |
|  | FD&C Green No. 3 (CI 42053) | FD&C Green No. 3 (1.0% Solution) | 0.005 |
|  | FD&C Yellow No. 5 (CI 19140) | FD&C Yellow No. 5 (1.0% Solution) | 0.007 |
| Part E | Menthol | Menthol Crystals, USP | 0.3 |
|  | Cinnamon (*Cinnamomum Cassia*) Oil, Grapefruit (*Citrus Grandis*) Oil, Orange (*Citrus Aurantium Dulcis*) Oil, Petitgrain (*Citrus Aurantium Amara*) Oil, Peppermint (*Mentha Piperita*) Oil, Eucalyptus Globulus Oil, Clove (*Eugenia Caryophyllus*) Oil, and Rosemary (*Rosmarinus Officinalis*) Oil | Essential Oil Blend #EE-50098 | 0.5 |
|  | Fragrance (Parfum) | Fragrance - Haarmann & Reimer #A40758/778926 | 0.3 |
|  |  |  | 100% |

UCARE Polymer JR-125 is commercially available from Amerchol Corp. of Edison, NJ;
PHYTRANTIOL and ETHYL PANTHENOL are commercially available from Roche Vitamins Inc. of Parsippany, NJ;
HAMPOSYL L-30 is commercially available from Hampshire of Lexington, MA;
HAMP-ENE 220 is commercially available from Akzo Nobel Inc. of Dobbs Ferry, NY;
PARAPEL LAM-100 is commercially available from Bernel Chemical Co. of Englewood, NJ;
AJIDEW N-50 is commercially available from Ajinomoto USA Inc. of Teaneck, NJ;
CROTEIN HKP is commercially available from Croda Inc. of Parsippany, NJ;
Saw Palmetto is commercially available from Chart at Patterson, NJ; and
FD&C Green No. 3 and Yellow No. 5 are commercially available from Hilton Davis Co. of Cincinnati, OH.

Deionized water may be metered into the processing tank and high speed mixing subsequently begun. Polyquaternium-10 and glycolic acid are added one at a time. Once the polymer is completely dispersed, the mixture is heated to 75° C. The remaining Part A ingredients are then added and mixed until all the solids are dissolved. The mixture is cooled to 60° C. and the Part B ingredients are added and mixed until uniform. The mixture is then cooled to 50° C. In a separate vessel, Part C is premixed until homogeneous, then added to the mixture of Parts A & B. Parts A, B, and C are mixed until uniform. The Part D ingredients are added and mixed until uniform, then cooled to 40° C. Premixed Part E is added and mixed until uniform, the Part F ingredients are added and mixed, and the composition is then cooled to 35° C. The appearance should be a light green, opaque, pearlized, semi-viscous liquid having a pH at 25° C. of between 5.4 to 6.1 and a viscosity between 6,000 to 12,000 cps (RVT: #5 @ 10 rpm @ 25° C.).

Example 3

Shampoo Formulation for Chemically Treated Hair

A pharmaceutical composition according to the invention may be formulated as a shampoo for protecting chemically treated hair as set forth below:

|  | Ingredient | Trade Name/Supplier | % by Weight |
|---|---|---|---|
| Part A | Deionized water | N/A | 86.4% |
|  | Polyquaternium-10 | UCARE Polymer JR-125 | 0.2 |
|  | Glycolic Acid | GLYPURE-70% Glycolic Acid | 0.1 |
|  | Tetrasodium Ethylene-Diamine-Tetraacetic Acid (EDTA) | HAMP-ENE 220 | 0.01 |
|  | Sodium Laureth Sulfate | STEOL CS-230 PCK | 10 |
|  | Glycol Stearate | LEXEMUL EGMS | 0.1 |
|  | Methylparaben | N/A | 0.05 |
|  | Sodium Lauroyl Sarcosinate | HAMPOSYL L-30 | 0.1 |
|  | Panthenol | Liquid DL-Panthenol 50% | 0.5 |
|  | Benzophenone-4 | UVINUL MS-40 | 0.05 |
| Part B | Disodium Cocoamphodiacetate | MIRANOL C2M CONC. NP | 1 |
| Part C | Lactamide Monoethanolamine (MEA) | PARAPEL LAM-100 | 0.5 |
|  | Sodium Peroxylinecarbolic Acid (PCA) | AJIDEW N-50 | 0.5 |
|  | Hair Keratin Amino Acids and Sodium Chloride | CROTEIN HKP | 0.05 |
|  | Laudimonium Hydroxypropyl Hydrolyzed Wheat Protein | HYDROTRITICUM QL | 0.01 |
| Part D | Methylchloroisothiazolinone and Methylisothiazolinone | KATHON CG | 0.05 |
|  | FD&C Red No. 40 (CI 16035) | FD&C Red No. 40 (1.0% Solution) | 0.02 |
| Part E | Jasmine (*Jasminum Officinale*) Oil, Palmarosa (*Cymbopogon Martini*) Oil, Sandalwood (*Santalum Album*) Oil, Patchouli (*Pogostemon Cablin*) Oil, Nutmeg (*Myristica Fragrans*) Oil, Grapefruit (*Citrus Grandis*) Oil, Orris (*Iris Florentina*) Root Oil, Carnation (*Dianthus Caryophyllus*) Oil | Essential Oil Blend "Passion" | 0.3 |
|  | Phytantriol | N/A | 0.02 |
| Part F | Glycolic acid | GLYPURE-70% glycolic acid | 0.1 |
| Part G | Deionized water | N/A | 0.1 |
|  | Sodium chloride | N/A | 0.1 |
|  |  |  | 100% |

HYDROTRITICUM QL is commercially available from Croda Inc. of Parsippany, NJ;
MIRANOL C2M is commercially available from Rhone-Poulenc N. American Chemicals of Cranbury, NJ;
Phytantriol is commercially available from Roche Vitamins Inc. of Parsippany, NJ; and
STEOL CS-230 PCK is commercially available from Stepan Co. of Northfield, IL.

Deionized water may be metered into the processing tank and high speed mixing subsequently begun. Polyquaternium-10 and glycolic acid are added one at a time. Once the polymer is completely dispersed, the mixture is heated to 75° C. The remaining Part A ingredients are then added and mixed until all the solids are dissolved. The mixture is cooled to 60° C. and the Part B ingredients are added and mixed until uniform. The mixture is then cooled to 50° C. Part C is then added to the mixture of Parts A & B and mixed until uniform. The Part D ingredients are added and mixed until uniform, then cooled to 40° C. Premixed Part E is added and mixed until uniform, the Part F ingredients are added in increments as need to obtain the desired pH of 5.7 to 6.5 and mixed until uniform. Then Part G is added in increments to obtain the desired viscosity of 8,000 to 12,000 cps (RVT#5 @ 10 rpm @ 25° C.), and the composition is then mixed and cooled to 35° C. The appearance should be a peach-colored, opaque, pearlized, semi-viscous liquid having a pH at 25° C. of between 5.7 to 6.5 and a viscosity between 8,000 to 12,000 cps (RVT: #5 @ 10 rpm @ 25° C.).

Example 4

Professional Scalp Formulation for Dandruff

A pharmaceutical composition according to the invention may be formulated in a more potent concentration as a shampoo for professional management of dandruff as set forth below:

|  | Ingredient | Trade Name/Supplier | % By Weight |
|---|---|---|---|
| Part A | Deionized water | N/A | 74.6% |
|  | Hydroxyethylcellulose | CELLOSIZE QP52,000H | 0.3 |
| Part B | Disodium Ethylene-Diamine-Tetraacetic Acid (EDTA) | HAMP-ENE $Na_2$ | 0.03 |
|  | Glycerin | Glycerine 99.5% | 1 |
|  | Glycolic Acid | GLYPURE-70% Glycolic Acid | 10 |

-continued

|  | Ingredient | Trade Name/Supplier | % By Weight |
|---|---|---|---|
| Part C | Deionized water | N/A | 1 |
|  | Sodium Hydroxide | Sodium Hydroxide, pellets (USP/NF) | 1 |
| Part D | Alcohol (denatured) | SD Alochol 40-B, Anhydrous | 10 |
|  | Salicylic Acid | Salicylic Acid, powder (USP/NF) | 1.8 |
| Part E | PPG-5-Ceteth-20 | PROCETYL AWS | 0.2 |
|  | Lemongrass (*Cymbopogon Schoenanthus*) Oil | Lemongrass Oil #65161 | 0.02 |
|  | Peppermint (*Mentha Piperita*) Oil | Peppermint Oil #097973-0594N | 0.04 |
|  | Geranium Maculatum Oil | Geranium Oil #01491 | 0.02 |
|  |  |  | 100% |

HAMP-ENE Na$_2$ is commercially available from Akzo Nobel Inc. of Dobbs Ferry, NY; and
PROCETYL AWS is commercially available from Croda Inc. of Parsippany, NJ.

Deionized water may be metered into the processing tank and high speed mixing subsequently begun. CELLOSIZE QP52, 000H is added and heated at 70° C until the solids are dissolved. The mixture is cooled to 40° C. The Part B ingredients are added and mixed until uniform. Premixed Part C is then added in increments to obtain the desired pH below, and mixed until uniform. The mixture is cooled to 25° C. and premixed part D is slowly added and mixed until uniform. Premixed Part E is added and mixed until uniform. The composition should be colorless, clear, semi-viscous liquid having a pH at 25° C. between 3.4 to 3.8 and a viscosity between 1,500 to 2,5000 cps (RVT#5 @ 10 rpm @ 25° C.)

Example 5

Scalp Formulation for Thinning Hair

A pharmaceutical composition according to the invention may be formulated as a shampoo for management of thinning hair as set forth below:

|  | Ingredient | Trade Name | % By Weight |
|---|---|---|---|
| Part A | Deionized water | N/A | 82.3% |
| Part B | Propylene Glycol | N/A | 5 |
|  | Methylparaben | N/A | 0.2 |
| Part C | Menthol | Menthol Crystals, USP | 0.03 |
|  | Ethyl Nicotinate |  | 0.05 |
|  | Cinnamon (*Cinnamomum Cassia*) Oil, Grapefruit (*Citrus Grandis*) Oil, Orange (*Citrus Aurantium Dulcis*) Oil, Petitgrain (*Citrus Aurantium Amara*) Oil | Essential Oil Blend #EE-50098 | 0.04 |
|  | Polysorbate 80 | TWEEN 80 | 3 |
|  | Phytantriol | Phytantriol | 0.2 |
|  | Biotin | N/A | 0.1 |
|  | Salicylic Acid | Salicylic Acid, powder, USP/NF | 0.5 |
|  | *Capsicum Frutescens* Extract and Safflower (*Carthamus Tinctorius*) Oil | Actiphyte of Capsicum, Lipo S | 0.05 |
| Part D | Allantoin | Allantoin | 0.5 |
|  | Tetrasodium EDTA | HAMP-ENE 220 | 0.2 |
|  | Lactamide Monoethanolamine | PARAPEL LAM-100 | 1.5 |
|  | Panthenyl Ethyl Ether | Ethyl Panthenol | 1.5 |
|  | Diazolidinyl Urea | GERMALL II | 0.3 |
|  | Cocamidopropyl PG-Dimonium Chloride Phosphate | PHOSPHOLIPID PTC | 1.08 |
|  | Saw Palmetto (*Sereno Serrulata*) Extract | Saw Palmetto Extract | 0.5 |
|  | Cyanocobalamin | Vitamin B$_{12}$ | 0.02 |
|  | Yeast Extract (Faex) | NAYAD S | 1 |
|  | Yeast Extract (Faex) | RESPIROGEN | 2 |
|  |  |  | 100% |

PHOSPHOLIPID PTC is commercially available from Mona Industries Inc. of Patterson, NJ; and
RESPIROGEN is commercially available from Immudyne, Inc. of Houston, TX.

Mix until uniform. Slowly add Part C to the batch. Mix until clear and homogeneous. Add Part B ingredients in the given order, mixing well after each addition. Mix until completely uniform. The resulting composition should be a light golden yellow, clear, non-viscous liquid having a pH at 25° C. of between 3.6 to 4.2.

Example 6

Conditioner Formulation for Thinning Hair

A pharmaceutical composition according to the invention may be formulated as a

Preparation Procedure

Meter deionized water into the processing tank. Start high speed mixing. Sprinkle-in CELLOSIZE Polymer PCG-10.When the Polymer is completely dispersed, heat to 75° C. Add the remaining Part A ingredientsw. Mix at 75° C. for 30 minutes until homogenous. Cool at 50° C. Add Part B ingredients. Mix until uniform. In a separate vessel, premix Part D until all the solids are dissovled. Add to the batch. Mix until uniform. Add Part E in increments as needed to obtain the desired pH. Continue mixing and cooling to 35° C. The resulting composition should have a very light green, opaque, semi-viscous appearance haveing a pH at 25° C. of between 3.8 to 4.5 and a viscosity between 7,000 to 11,000 cPs (RVT: #4 @ 10 rpm @ 25° C.).

| | Ingredient | Trade Name | % By Weight |
|---|---|---|---|
| Part A | Deionized water | N/A | 79.5% |
| | Hydroxyethylcellulose | CELLOSIZE POLYMER PCG-10 | 1 |
| | Methylparaben | N/A | 0.2 |
| | Benzophenone-4 | UVINUL MS-40 | 0.1 |
| | Glyceryl Stearate | RITA GMS-55G | 2 |
| | Stearalkonium Chloride | MAQUAT SC-18 85% | 2 |
| | Cetyl Alcohol | LANETTE 16 | 2.5 |
| | Stearyl Alcohol | LANETTE 18 | 2.5 |
| | Glycerin | Glycerine 99.5% | 1 |
| Part B | Laurdimonium Hydroxypropyl Hydrolyzed Wheat Protein | HYDROTRITICUM QL | 1 |
| | Panthenol | DL-PANTHENOL 50% | 1 |
| | Hydrolyzed Soy Protein | HYDROSOY 2000 SF | 1 |
| | Hydrolyzed Wheat Protein Hydroxypropyl Polysiloxane | CRODASONE W | 1 |
| | Hair Keratin Amino Acids and Sodium Chloride | CROTEIN HKP Powder | 1 |
| Part C | Methylchloroisothiazolinone and Methylisothiazolinone | KATHON CG | 0.05 |
| | Benzalkonium Chloride | BTC-50 | 0.5 |
| | Biotin | Biotin | 0.05 |
| | Ethyl Nicotinate | Ethyl Nicotinate | 0.05 |
| | Witch Hazel (*Hamamelis Virginiana*) Distillate | Witch Hazel Distillate E02 | 2 |
| | FD&C Blue No. 1 (CI 42090) | FD&C Blue No. 1 (1.0% Solution) | 0.006 |
| | FD&C Yellow No. 5 (CI 19140) | FD&C Yellow No. 5 (1.0% Solution) | 0.006 |
| Part D | Cinnamon (*Cinnamomum Cassia*) Oil, Grapefruit (*Citrus Grandis*) Oil, Orange (*Citrus Aurantium Dulcis*) Oil, Petitgrain (*Citrus Aurantium Amara*) Oil, Peppermint (*Mentha Piperita*) Oil, *Eucalyptus Globulus* Oil, Clove (*Eugenia Caryophyllus*) Oil, Rosemary (*Rosmarinus Officinalis*) Oil | Essential Oil Blend #EE-50098 | 0.1 |
| | Menthol | Menthol Crystals, USP | 0.5 |
| | Fragrance (Parfum) | Fragrance - HAARMANN & REIMER #A40758/778926 | 0.5 |
| Part E | Glycolic Acid | GLYPURE-70% Glycolic Acid | 0.5 |
| | | | 100% |

CRODASONE W is commercially available from Croda Inc. of Parsippany, NJ.

Example 7

Professional Scalp Treatment for Chemically Treated Hair

A pharmaceutical composition according to the invention may be formulated in a higher concentration of acid as a professional treatment for protection of chemically treated hair as set forth below:

|  | Ingredient | Trade Name | % By Weight |
|---|---|---|---|
| Part A | Deionized water | N/A | 73% |
|  | Hydroxyethylcellulose | CELLOSIZE QP52,000H | 1 |
| Part B | Disodium EDTA | HAMP-ENE Na$_2$ | 0.2 |
|  | Glycerin | Glycerine 99.5% | 5 |
|  | Panthenol | Liquid DL-Panthenol 50% | 1 |
|  | Quaternium-75 | FINQUAT CT | 1.5 |
|  | Cetrimonium Chloride | CARSOQUAT CT-429 | 1.5 |
|  | Glycolic Acid | GLYPURE-70% Glycolic Acid | 12 |
| Part C | Deionized water | N/A | 2 |
|  | Sodium Hydroxide | Sodium Hydroxide, pellets, USP/NF | 1.5 |
| Part D | PPG-5-Ceteth-20 | PROCETYL AWS | 1 |
|  | Phytantriol |  | 0.2 |
|  | Ylang Ylang (*Cananga Odorata*) Oil | Ylang Ylang Oil #65040 | 0.04 |
|  | Jasmine (*Jasminum Officinale*) Oil | Jasmine Oil #65072 | 0.01 |
|  | Chamomile (*Anthemis Nobilis*) Oil | Chamomile Oil #112528-0395N | 0.02 |
|  |  |  | 100% |

FINQUAT CT is commercially available from Finetex Inc. of Elmwood Park, NJ.

Preparation Procedure

Meter deionized water into the processing tank. Start high speed mixing. Sprinkle-in CELLOSIZE QP52, 000H. Heat to 70° C. Mix until all the solids are completely dissolved, and the batch is clear and uniform. Cool to 40° C. Add Part B ingredients. Mix until uniform. Slowly add premixed Part C ingredients in increments as needed to obtain the desired pH. Mix until uniform. Add premixed Part D. Continue mixing and cooling to 35° C. The resulting composition should be a colorless to pale straw-colored, clear, semi-viscous liquid having a pH at 25° C. of between 3.4 to 3.8 and a viscosity between 2,500 to 3,500 cPs (RVT: #3 @ 10 rpm @ 25° C.).

Example 8

Professional Scalp Management of Thinning Hair

A pharmaceutical composition according to the invention may be formulated in a higher concentration of acid for professional management of thinning hair as set forth below:

|  | Ingredient | Trade Name | % By Weight |
|---|---|---|---|
| Part A | Deionized water | N/A | 77.5% |
|  | Hydroxyethylcellulose | CELLOSIZE QP52,000H | 1 |
| Part B | Disodium EDTA | HAMP-ENE Na$_2$ | 0.2 |
|  | Glycerin | Glycerine 99.5% | 5 |
|  | Panthenyl Ethyl Ether | Ethyl Panthenol | 1 |
|  | Glycolic Acid | GLYPURE-70% Glycolic Acid | 12 |
| Part C | Deionized water | N/A | 1.8 |
|  | Sodium Hydroxide | Sodium Hydroxide, pellets, USP/NF | 1 |
| Part D | PPG-5-Ceteth-20 | PROCETYL AWS | 0.2 |
|  | Phytantriol | Phytantriol | 0.2 |
|  | Ethyl Nicotinate | Ethyl Nicotinate | 0.05 |
|  | Menthol | Menthol Crystals, USP | 0.03 |
|  | Cinnamon (*Cinnamomum Cassia*) Oil | Cinnamon Oil #65028 | 0.02 |
|  | Rosemary (*Rosmarinus Officinalis*) Oil | Rosemary Oil #65138 | 0.03 |
|  | Peppermint (*Mentha Piperita*) Oil | Peppermint Oil #097973-0594N | 0.02 |
|  |  |  | 100% |

Preparation Procedure

Meter deionized water into the processing tank. Start high speed mixing. Sprinkle-in Cellosize QP52,000H. Heat to 70° C. Mix until all the solids are completely dissolved, and the batch is clear and uniform. Cool to 40° C. Add Part B ingredients. Mix until uniform. Slowly add premixed Part C in increments as needed to obtain the desired pH. Mix until uniform. Add premixed Part D. Continue mixing and cooling to 35° C. The resulting composition should be a colorless to pale straw-colored, clear, semi-viscous liquid having a pH at 25° C. between 3.4 to 3.8 and a viscosity between 2,200 to 3,500 cPs (RVT: #3 @ 10 rpm @ 25° C.).

Example 9

Conditioner for Chemically Treated Hair

A pharmaceutical composition according to the invention may be formulated as a conditioner for chemically treated hair as set forth below:

|  | Ingredient | Trade Name | % By Weight |
|---|---|---|---|
| Part A | Deionized water | N/A | 88% |
|  | Guar Hydroxypropyltrimonium Chloride | JAGUAR C-13S | 0.5 |
|  | Glycolic Acid | GLYPURE-70% Glycolic Acid | 0.15 |
|  | Methylparaben | N/A | 0.15 |
|  | Stearalkonium Chloride | MAQUAT SC-18 85% | 2 |
|  | Cetyl Alcohol | LANETTE 16 | 2 |
|  | Stearyl Alcohol | LANETTE 18 | 2 |
|  | Trimethylsilylamodimethicone | SF 1708-D1 | 0.5 |
|  | Sodium PCA | AJIDEW N-50 | 0.05 |
|  | Benzophenone-4 | UVINUL MS-40 | 0.1 |
| Part B | Hydrolyzed Wheat Protein and Hydrolyzed Wheat Starch | CROPEPTIDE W | 0.1 |
|  | Hydrolyzed Wheat Protein Hydroxypropyl Polysiloxane | CRODASONE W | 0.5 |
|  | Panthenol | Liquid DL-Panthenol 50% | 1 |
|  | Hydrolyzed Soy Protein | HYDROSOY 2000 SF | 1 |
|  | Phytantriol | Phytantriol | 0.3 |
|  | Polyquaternium-11 | GAFQUAT 755N | 1 |
| Part C | Methylchloroisothiazolinone and Methylisothiazolinone | KATHON CG | 0.05 |
|  | Benzalkonium Chloride | BTC-50 | 0.3 |
|  | FD&C Red No. 40 (C1 16035) | FD&C Red No. 40 (1.0% Solution) | 0.012 |
|  | Jasmine (*Jasminum Officinale*) Oil, Palmarosa (*Cymbopogon Martini*) Oil, Sandalwood (*Santalum Album*) Oil, Patchouli (*Pogostemon Cablin*) Oil, Nutmeg (*Myristica Fragrans*) Oil, Grapefruit (*Citrus Grandis*) Oil, Orris (*Iris Florentina*) Root Oil, Carnation (*Dianthus Caryophyllus*) Oil | Essential Oil Blend "Passion" | 0.3 |
|  |  |  | 100% |

GAFQUAT 775N is commercially available from ISP Corp. of Bound Brook, NJ.

Preparation Procedure

Meter deionized water into the processing tank. Start high speed mixing. Sprinkle-in Jaguar C-13S. Add Glypure. When the Jaguar is completely dispersed, heat to 75° C. Add the remaining Part A ingredients. Mix at 75° C. for 30 minutes until homogeneous. Cool to 50° C. Add Part B ingredients. Mix until uniform. Cool to 40° C. Add Part C ingredients. Continue mixing and cooling to 35° C. The resulting composition should be light peach-colored, opaque, semi-viscous, having a pH at 25° C. between 4 to 4.8 and a viscosity between 8,000 to 12,000 cPs (RVT: #4 @ 10 rpm @ 25° C.).

Various modifications of the invention in addition to those shown and described herein will be apparent to those skilled in the art from the foregoing description. Such modifications are also intended to fall within the scope of the appended claims. The foregoing disclosure includes all the information deemed essential to enable those skilled in the art to practice the claimed invention.

What is claimed is:

1. A method of treating an infectious or scaling scalp condition which comprises topically applying to the scalp of a patient in need thereof a therapeutically effective amount of each of an acidic component which is a hydroxy acid, or a pharmaceutically acceptable salt thereof, a vitamin A component, and an anti-growth agent to inhibit fungus, or yeast, or a mixture thereof.

2. The method of claim 1, wherein the scalp condition treated is at least one of dandruff, seborrheic dermatitis, psoriasis, or folliculitis.

3. The method of claim 1, wherein the applying is by at least one of a shampoo, aerosol spray, gel, paste, cream, lotion, sponge, emulsion, or ointment.

4. The method of claim 1, wherein about 1 mg to 10,000 mg of the acidic component, vitamin A component, and anti-growth agent are together administered.

5. The method of claim 1, wherein the acidic component, vitamin A component, and anti-growth agent are administered concurrently.

6. The method of claim 1, wherein the acidic component, vitamin A component, and anti-growth agent are administered concurrently with at least one additional pharmaceutical composition for the prevention or treatment of the scalp condition.

7. The method of claim 1, which further comprises administering at least one of a surfactant, stabilizer, preservative, moisturizer, anti-inflammatory agent, antioxidant, or coloring agent.

8. The method of claim 1, wherein the acidic component comprises an alpha-hydroxy acid or beta-hydroxy acid, the vitamin A component comprises retinyl palmitate, and the anti-growth agent comprises at least one of triclosan or clotrimazole.

* * * * *